United States Patent [19]

Scholten et al.

[11] Patent Number: 4,748,241

[45] Date of Patent: May 31, 1988

[54] PROCESS FOR PRODUCING AQUEOUS N-METHYLMORPHOLINE-N-OXIDE SOLUTIONS

[75] Inventors: Heinz Scholten, Haltern; Klaus Rindtorff, Recklinghausen, both of Fed. Rep. of Germany

[73] Assignee: Hüls Aktiengesellschaft, Marl, Fed. Rep. of Germany

[21] Appl. No.: 11,526

[22] Filed: Feb. 6, 1987

[30] Foreign Application Priority Data

May 31, 1986 [DE] Fed. Rep. of Germany ....... 3618352

[51] Int. Cl.$^4$ .......................................... C07D 295/22
[52] U.S. Cl. ................................................... 544/173

[58] Field of Search ........................................ 544/173

[56] References Cited

U.S. PATENT DOCUMENTS 3,447,939 6/1969 Johnson ................................ 536/58

Primary Examiner—Robert W. Ramsuer
Attorney, Agent, or Firm—Gilbert L. Wells

[57] ABSTRACT

N-methylmorpholine-N-oxide is prepared by reacting the azeotrope of methylmorpholine and water with an aqueous solution of hydrogen peroxide. The reaction solution product is thereupon concentrated to the desired content in N-methylmorpholine-N-oxide.

6 Claims, No Drawings

PROCESS FOR PRODUCING AQUEOUS N-METHYLMORPHOLINE-N-OXIDE SOLUTIONS

CROSS-REFERENCE TO A RELATED APPLICATION

Applicants claim priority under 35 USC 119 for Application P 36 18 352.0, filed May 31, 1986, in West Germany.

BACKGROUND OF THE INVENTION

The field of the invention is the production of synthetic resins having a six membered nitrogen ring with at least one diverse hetero atom and the invention is particularly concerned with the production of aqueous solutions of N-methylmorpholine-N-oxide.

U.S. Pat. No. 3,447,939 discloses the state of the art of using aqueous solutions of N-methylmorpholine-N-oxide and this disclosure is incorporated herein by reference.

N-methylmorpholine-N-oxide is shown by the disclosure of U.S. Pat. No. 3,447,939 to be a good solvent for cellulose and therefore is exceedingly well suited to the production of fibers.

Cellulose fibers made with N-methylmorpholine-N-oxide are characterized by improved tear resistance over conventional fibers.

Further applications of N-methylmorpholine-N-oxide are by-products for pharmaceutics. Because N-methylmorpholine-N-oxide evinces only a moderate storage stability and because as a pure substance it tends toward oxygen separation, the preferred commercial form is a 60% aqueous solution and furthermore it is used in this 60% aqueous solution.

However, storage stability and various applications require high solution purity. Contaminations which have been typically found and which degrade the storage stability or interfere in the application of N-methylmorpholine-N-oxide include N-methylmorpholine, peroxides and acid components. The impurities in the commercial products are noticeable by a deep yellow color.

The impurities can be detected analytically. Illustrative in the potentiometric titration of commercial N-methylmorpholine-N-oxide with hydrochloric acid and soda lye, two potential jumps are noted, which can be related to free methylmorpholine and carboxyl groups. Furthermore, peroxides are ascertained by iodometric titration, which because eluding precise identification, are calculated as being hydrogen peroxide.

Commercial N-methylmorpholine-N-oxide contains up to 1% by weight of methylmorpholine, up to 0.01% by weight of peroxides calculated as hydrogen peroxide, and up to 0.2% by weight of carboxyl groups. If according to the state of the art approximately equimolar amounts of (35%) hydrogen peroxide and (99%) commercial methylmorpholine are made to react, then there occurs a 57.4% solution of methylmorpholine-N-oxide comprising in its impurities 0.3% by weight of peroxide (calculated as $H_2O_2$), 0.97% by weight of methylmorpholine and 0.3% by weight of carboxyl groups. After this solution is concentrated to the commercial solution of 60% by weight of methylmorpholine-N-oxide, the concentration of the impurities increases further, and therefore the product does not correspond to the state of the art. Because most of all the peroxide content is excessive, the literature suggests dissociating it by adding 0.1% by weight of catalase. This catalase, however, represents a further contaminant requiring in turn a subsequently costly purification comprising the following steps:

1. Removal of the water by azeotropic distillation with benzene.
2. Separating the methylmorpholine-N-oxide phase from the benzene.
3. Precipitating the methylmorpholine-N-oxide using acetone.
4. Filtering and vacuum-drying the methylmorpholine-N-oxide.
5. Preparing the solution.

This is a very costly procedure.

SUMMARY OF THE INVENTION

Having in mind the limitations of the prior art there is a need for a simple and more economical manner for production of pure, aqueous solutions of N-methylmorpholine-N-oxide solutions.

This need is met by a process for producing an aqueous, pure solution of N-methylmorpholine-N-oxide wherein methylmorpholine is reacted with an aqueous solution of hydrogen peroxide. Mixtures of methylmorpholine and water are distilled to form an azeotrope and the methylmorpholine/water azeotrope is reacted with an aqueous solution of hydrogen peroxide at temperatures between 60° and 100° C. The reaction solution is subsequently concentrated to the desired content in N-methylmorpholine-N-oxide.

Surprisingly it was discovered that an N-methylmorpholine-N-oxide solution of high purity is achieved if first the initial product, i.e., methylmorpholine, is mixed with water, whereupon this mixture is distilled and then the top product, i.e., the azeotrope, is reacted with hydrogen peroxide, the reaction product so obtained being concentrated by partial distillation, preferably to a concentration of about 60% by weight.

The methylmorpholine/water azeotrope contains 60 to 80 percent by weight methylmorpholine.

DESCRIPTION OF THE PREFERRED EMBODIMENTS

Preferably the mixtures of methylmorpholine and water contain 50 to 75% methylmorpholine and 25 to 50% water. In particular, mixtures of 50% methylmorpholine and 50% water are used. Methylmorpholine and hydrogen peroxide are preferably used in a molar ratio of 1/0.9 to 1/0.75. The reaction between methylmorpholine and hydrogen peroxide takes place at temperatures between 60° and 100° C., preferably between 70° and 75° C. As a rule the reaction time is 4 to 6 hours. The secondary reaction as a rule takes place at the same temperature. The hydrogen peroxide used generally is of a concentration of 30 to 65 and preferably of 30 to 35% by weight.

The process furthermore is optimally operated continuously, with the option of monitoring the end product concentration, preferably about 60% by weight, by means of the index of refraction or density measurements. The solution of N-methylmorpholine-N-oxide so prepared is only slightly tinged yellow and its impurities, namely peroxides, methylmorpholine and carboxyl groups, can hardly be detected. It is useful directly in all applications.

EXAMPLE 600 grams of methylmorpholine and 600 grams of water are distilled at a reflux ratio of 1 through a 2-meter packed column. 705 g of azeotrope are collected at the top. The azeotrope product contains 74.5% methylmorpholine.

680 g of the methylmorpholine-azeotrope are reacted with stirring at 70° C. within 2 hours with 400 grams of (35%) hydrogen peroxide and then are stirred further for 6 hours at 68° C. This product then is vacuum-concentrated to 803 grams. The following aqueous N-methylmorpholine-N-oxide solution is obtained:

| N—methylmorpholine-N—oxide | 59.4% |
| --- | --- |
| peroxide (calculated as $H_2O_2$) | 2 ppm |
| methylmorpholine | 0.1% |
| acid number | 0.1 mg KOH/gram. |

The water that is distilled off contains 34% by weight of methylmorpholine. After concentration by distillation, it is reused.

COMPARISON TEST ACCORDING TO U.S. PAT. NO. 3,447,939

(This Comparison test was modified to the extent that the dissociation of the excess peroxide was dispensed with and that the concentration took place as in the above Example.)

650 grams of N-methylmorpholine and 50 grams of water are heated in a three-neck flask to 68° C., whereupon 485 grams of a 35% solution of hydrogen peroxide are added at 70° C. within 2 hours. Upon complete addition, the reaction mixture is further kept for 2 hours at a temperature of 68° to 70° C., and thereupon concentrated in vacuum to 974 grams at 70° C. The following deeply yellow-brown solution is obtained:

| N—methylmorpholine-N—oxide | 59% |
| --- | --- |
| peroxide (calculated as $H_2O_2$) | 0.21% |
| methylmorpholine | 0.24% |
| acid number | 5.3 mg KOH/gram. |

We claim:

1. In a process for producing an aqueous, pure solution of N-methylmorpholine-N-oxide by reacting methylmorpholine with an aqueous solution of hydrogen peroxide, the improvement comprising:
   preparing mixtures of methylmorpholine and water, distilling said mixtures of methylmorpholine and water to form an azeotrope of methylmorpholine/water, reacting said azeotrope with an aqueous solution of hydrogen peroxide at temperatures between 60° and 100° C. to form a reaction product and subsequently concentrating said reaction solution to a given content in N-methylmorpholine-N-oxide.

2. The process of claim 1, wherein said methylmorpholine and said hydrogen peroxide are used in a molar ratio between 1/0.9 and 1/0.75.

3. The process of claim 2, wherein said reaction product is obtained at a temperature between 70° and 75° C.

4. The process of claim 3, wherein said aqueous solution of hydrogen peroxide is 30 to 65% hydrogen peroxide by weight.

5. The process of claim 4, wherein said mixtures of methylmorpholine and water are 50 to 75% by weight methylmorpholine and 25 to 50% by weight water.

6. The process of claim 5, wherein said mixtures of methylmorpholine and water are 50% by weight methylmorpholine and 50% by weight water.

* * * * *